(12) United States Patent
Vogel

(10) Patent No.: US 6,727,329 B2
(45) Date of Patent: Apr. 27, 2004

(54) SALTS OF LEWIS ACID/ACID ADDUCTS AND CATALYST ACTIVATORS THEREFROM

(75) Inventor: Alexander Vogel, Houston, TX (US)

(73) Assignee: Dow Global Technology Inc., Midland, MI (US)

( * ) Notice: Subject to any disclaimer, the term of this patent is extended or adjusted under 35 U.S.C. 154(b) by 0 days.

(21) Appl. No.: 10/164,099

(22) Filed: Jun. 4, 2002

(65) Prior Publication Data

US 2003/0032549 A1 Feb. 13, 2003

Related U.S. Application Data

(60) Provisional application No. 60/307,249, filed on Jul. 23, 2001.

(51) Int. Cl.$^7$ .............................. C08F 4/44; B01J 31/38
(52) U.S. Cl. ...................... 526/127; 526/161; 526/171; 526/172; 526/901; 502/152; 502/155
(58) Field of Search ................................ 502/152, 155; 526/161, 171, 172, 901

(56) References Cited

U.S. PATENT DOCUMENTS

| | | |
|---|---|---|
| 5,132,380 A | 7/1992 | Stevens et al. |
| 5,153,157 A | 10/1992 | Hlatky et al. |
| 5,189,192 A | 2/1993 | LaPointe et al. |
| 5,198,401 A | 3/1993 | Turner et al. |
| 5,321,106 A | 6/1994 | LaPointe et al. |
| 5,350,723 A | 9/1994 | Neithamer et al. |
| 5,407,884 A | 4/1995 | Turner et al. |
| 5,447,895 A | 9/1995 | Marks et al. |
| 5,470,927 A | 11/1995 | Turner et al. |
| 5,625,087 A | 4/1997 | Devore et al. |

FOREIGN PATENT DOCUMENTS

| | | |
|---|---|---|
| EP | 520732 | 12/1992 |
| WO | WO99/42467 | 8/1999 |
| WO | WO01/23442 | 4/2001 |
| WO | WO02/08303 | 1/2002 |

OTHER PUBLICATIONS

Marks, et al., in J. Am. Chem. Soc., 118, 12451–12452 (1996).

*Primary Examiner*—Robert Harlan

(57) ABSTRACT

A compound useful as a cocatalyst or cocatalyst component, especially for use as an addition polymerization catalyst compound, corresponding to the formula: $(A^{*hu +a})_b (Z^*J^*_j)^{-c}_d$, wherein:

A* is a proton or a cation of from 1 to 80 atoms, preferably 1 to 60 atoms, not counting hydrogen atoms, said A* having a charge +a;

Z* is an anion group of from 1 to 50 atoms, preferably 1 to 30 atoms, not counting hydrogen atoms, further containing two or more Lewis base sites, said Z* being the conjugate base of an inorganic Bronsted acid or a carbonyl- or non-cyclic, imino-group containing organic Bronsted acid;

J* independently each occurrence is a Lewis acid of from 1 to 80 atoms, preferably 1 to 60 atoms, not counting hydrogen atoms, coordinated to at least one Lewis base site of Z*, and optionally two or more such J* groups may be joined together in a moiety having multiple Lewis acidic functionality;

j is a number from 1 to 12; and a, b, c, and d are integers from 1 to 3, with the proviso that a×b is equal to c×d.

15 Claims, No Drawings

SALTS OF LEWIS ACID/ACID ADDUCTS AND CATALYST ACTIVATORS THEREFROM

CROSS REFERENCE STATEMENT

This application claims the benefit of U.S. Provisional Application No. 60/307,249, filed Jul. 23, 2001.

BACKGROUND INFORMATION

The present invention relates to compounds that are useful as catalyst components. More particularly the present invention relates to such compounds that are particularly adapted for use in the coordination polymerization of unsaturated compounds comprising an anion containing at least two Lewis basic sites derived from certain inorganic or organic Bronsted acids, which are coordinated to Lewis acids. Such compounds are particularly advantageous for use in forming supported polymerization catalysts wherein at least the catalyst activator is chemically attached to a substrate material.

It is previously known in the art to activate Ziegler-Natta polymerization catalysts, particularly such catalysts comprising Group 3–10 metal complexes containing delocalized π-bonded ligand groups, by the use of Bronsted acid salts capable of transferring a proton to form a cationic derivative or other catalytically active derivative of such Group 3–10 metal complex. Preferred Bronsted acid salts are such compounds containing a cation/anion pair that is capable of rendering the Group 3–10 metal complex catalytically active. Suitable activators comprise fluorinated arylborate anions, such as tetrakis(pentafluorophenyl)borate. Additional suitable anions include sterically shielded diboron anions of the formula:

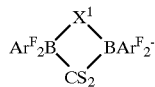

wherein:

S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895. Additional examples include carborane compounds such as are disclosed and claimed in U.S. Pat. No. 5,407,884.

Examples of preferred charge separated (cation/anion pair) activators are ammonium, sulfonium, or phosphonium salts capable of transferring a hydrogen ion, disclosed in U.S. Pat. Nos. 5,198,401, 5,132,380, 5,470,927 and 5,153,157, as well as oxidizing salts such as ferrocenium, silver or lead salts, disclosed in U.S. Pat. Nos. 5,189,192 and 5,321,106 and strongly Lewis acidic salts such as carbonium or silylium salts, disclosed in U.S. Pat. Nos. 5,350,723 and 5,625,087.

Further suitable activators for the above metal complexes include strong Lewis acids including tris(perfluorophenyl)borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996).

In WO99/42467, WO01/23442 and WO02/08303 expanded ionic catalyst activators are disclosed that are well suited for use as olefin polymerization activators.

Despite the satisfactory performance of the foregoing catalyst activators under a variety of polymerization conditions, there is still a need for improved cocatalysts for use in the activation of various metal complexes especially under a variety of reaction conditions. Accordingly, it would be desirable if there were provided compounds that could be employed in solution, slurry, gas phase or high pressure polymerizations and under homogeneous or heterogeneous process conditions having improved activation properties.

SUMMARY OF THE INVENTION

According to the present invention there are now provided compounds useful as catalyst activators corresponding to the formula: $(A^{*+a})_b(Z^{*J*}_j)^{-c}_d$, wherein:

$A^*$ is a proton or a cation of from 1 to 80 atoms, preferably 1 to 60 atoms, not counting hydrogen atoms, said $A^*$ having a charge +a, $Z^*$ is an anion group of from 1 to 50 atoms, preferably 1 to 30 atoms, not counting hydrogen atoms, further containing two or more Lewis base sites, said $Z^*$ being the conjugate base of an inorganic Bronsted acid or a carbonyl- or non-cyclic, imino-group containing organic Bronsted acid;

$J^*$ independently each occurrence is a Lewis acid of from 1 to 80 atoms, preferably 1 to 60 atoms, not counting hydrogen atoms, coordinated to at least one Lewis base site of $Z^*$, and optionally two or more such $J^*$ groups may be joined together in a moiety having multiple Lewis acidic functionality;

j is a number from 1 to 12; and a, b, c, and d are integers from 1 to 3, with the proviso that a×b is equal to c×d.

The foregoing compounds may be utilized in combination with one or more Group 3–10 or Lanthanide metal complexes to form catalyst compositions for polymerization of addition polymerizable monomers, especially ethylenically unsaturated monomers, most preferably, $C_{2\text{-}20,000}$ α-olefins. Additionally, the compounds may be utilized to form latent activators, that is, compounds that may themselves not cause a metal complex to become catalytically active due, for example, to the presence of a reactive group such as a hydroxyl group, but which may be converted to an active compound by, for example, in-situ reaction of the hydroxyl group with a Lewis acid, especially an aluminum hydrocarbyl compound, or an alkali metal halide or ammonium halide salt. Moreover, such compounds may be deposited onto solid supports, such as by impregnation, surface deposition, physisorption or chemical reaction with the support, reactive functionality of the support, or chemical modifiers associated with the support, to form heterogeneous catalyst components for use in preparing heterogeneous catalyst compositions for use in polymerization of the foregoing monomers.

Thus, in one embodiment of the invention, the foregoing compounds containing hydroxyl or other reactive functionality are used to form supported catalyst components by reaction of the hydroxyl group thereof with reactive functionality of a support material, or by conversion of the dialkylaluminumoxyhydrocarbyl, trihydrocarbylsiloxyhydrocarbyl or hydrocarbyloxyhydrocarbyl group to a reactive functionality and reaction thereof with reactive functionality of a support material. The resulting supported catalyst components are highly resistant to loss of activator compound in a liquid reaction medium such as occurs in a slurry polymerization. One or more Group 3–10 or Lanthanide metal complexes, preferably a Group 4 metal complex, and additional additives, modifiers and adjuvants may be added to the catalyst component, either before, after or simultaneous with addition of the cocatalyst of the present invention, to form the fully formulated catalyst composition. Accordingly, in one embodiment of the invention the foregoing structures can be created on a surface containing chemically or physically bonded anionic groups, Z*.

Another embodiment of the invention is a composition of matter comprising the admixture or reaction product, optionally in an inert diluent, of an inorganic Bronsted acid or a carbonyl- or non-cyclic, imino-group-containing organic Bronsted acid; from one to twelve moles per mole of Bronsted acid of a Lewis acid having from 1 to 80, preferably 1 to 60 atoms, not counting hydrogen atoms; optionally a Lewis base of from 1 to 80, preferably 1 to 60 atoms, not counting hydrogen, preferably an amine or phosphine containing Lewis base; and further optionally an organoaluminum compound, preferably an alumoxane, especially methylalumoxane or modified methylalumoxane.

Additionally according to the present invention there is provided a catalyst composition for polymerization of an ethylenically unsaturated, polymerizable monomer comprising, in combination, the above described activator compound or composition of matter, a Group 3–10 metal complex that is capable of activation to form an addition polymerization catalyst, or the reaction product of such combination, and optionally a support.

Additionally according to the present invention there is provided a process for polymerization of one or more ethylenically unsaturated, polymerizable monomers comprising contacting the same, optionally in the presence of an inert aliphatic, alicyclic or aromatic hydrocarbon, with the above catalyst compositions or supported catalyst compositions.

The foregoing compounds are uniquely adapted for use in activation of a variety of metal complexes, especially Group 4 metal complexes, under standard and a typical olefin polymerization conditions. Because of this fact, the foregoing compounds are capable of forming highly desirable olefin polymers in high efficiency. Especially desirably, the compounds are readily hydrolyzed and are easily removed from the polymer product after polymerization.

DETAILED DESCRIPTION OF THE INVENTION

All references herein to elements belonging to a certain Group refer to the Periodic Table of the Elements published and copyrighted by CRC Press, Inc., 1999. Also any reference to the Group or Groups shall be to the Group or Groups as reflected in this Periodic Table of the Elements using the IUPAC system for numbering groups. For purposes of United States patent practice, the contents of any patent, patent application or publication referenced herein are hereby incorporated by reference in their entirety herein, especially with respect to the disclosure of structures, synthetic techniques and general knowledge in the art. The term "comprising" and derivatives thereof, when used herein with respect to a composition, mixture, or sequence of steps, is not intended to exclude the additional presence of any other compound, component or event.

The catalyst activators of the invention are further characterized in the following manner. $A^{*+a}$ is desirably chosen to provide overall neutrality to the compound and to not interfere with subsequent catalytic activity. Moreover, the cation may participate in the formation of the active catalyst species, desirably through a proton transfer, oxidation, or ligand abstraction mechanism, or a combination thereof. Additionally, certain cations beneficially improve the solubility of the resulting activator in particular reaction media under use conditions. For example, in the homopolymerization or copolymerization of aliphatic olefins, particularly in the solution phase, an aliphatic diluent is commonly used. Accordingly, cationic species that are relatively soluble in such reaction media, or render the catalyst activator more soluble therein are highly preferred.

Examples of suitable cations include: ammonium, sulfonium, phosphonium, oxonium, carbonium, and silylium cations, preferably those containing up to 80 atoms not counting hydrogen, a proton, as well as ferrocenium, $Ag^+$, $Pb^{+2}$, or similar oxidizing cations. In a preferred embodiment, a, b, c and d are all equal to one.

Preferred $A^{*+a}$ cations are protons, and ammonium cations, especially trihydrocarbyl-substituted ammonium cations. Examples include trimethylammonium-, triethylammonium-, tripropylammonium-, tri(n-butyl)ammonium-, methyldi($C_{14-18}$ alkyl)ammonium-, dimethyl ($C_{14-18}$ alkyl)ammonium-, N,N-dimethylanilinium-, N,N-diethylanilinium-, N,N-dimethyl(2,4,6-trimethylanilinium)-, N,N-di(tetradecyl)lanilinium-, N,N-di(tetradecyl)-2,4,6-trimethylanilinium)-, N,N-di(octadecyl)lanilinium-, N,N-di(octadecyl)-2,4,6-trimethylanilinium)-, and methyldicyclohexylammonium-cations.

More preferred cations include those containing one or two $C_{10}$–$C_{40}$ alkyl groups, such as methylbis(octadecyl)ammonium-, dimethyloctadecylammonium-, methylbis(tetradecyl)ammonium-, bis(octadecyl)anilinium-, and bis(octadecyl)-3,5-dimethylanilinium-cations. It is further understood that the cation may comprise a mixture of hydrocarbyl groups of differing lengths. For example, the protonated ammonium cation derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Preferably Z* is the conjugate base of an inorganic acid and is selected from the group consisting of: $NO_3^-$, $PO_4^{3-}$, $SO_4^{2-}$, $RSO_3^-$ and $CO_3^{2-}$, or Z* is the conjugate base of an organic acid and is selected from the group consisting of: $[RC(O)O]^-$, $[RC(NR)NR]^-$, $[R'C(O)CRC(O)R']^-$, $[(R'C(O))_3C]^-$, $[RC(NR)CRC(NR)R]^-$, and $[(RC(NR))_3C]^-$, wherein each R is independently a hydrogen-; hydrocarbyl-; or halocarbyl-group; a hydrocarbyl group further substituted with one or more carbonyl-, halo-, hydroxy-, dialkylamino-, dialkylaluminumoxy-, trihydrocarbylsilyl-, trihydrocarbylsiloxy-, or hydrocarbyloxy-groups; or a halocarbyl group further substituted with one or more carbonyl-, hydroxy-, dialkylamino-, dialkylaluminumoxy-, trihydrocarbylsilyl-, trihydrocarbylsiloxy-, or hydrocarbyloxy-groups; and each R' is independently R or two R' groups may be joined together thereby forming a divalent group.

More preferably, Z* is an acetylacetonate, cyclohexa-1,3-dionate, $[RC(O)O]^-$ or $NO_3^-$, wherein R is a $C_{6-24}$ hydrocarbyl group, most preferably a $C_{12-24}$ alkyl group, or the conjugate base anion derived from indane-1,3-dione or methyltriacetyl corresponding to the following structure:

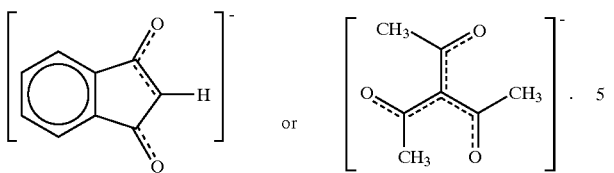

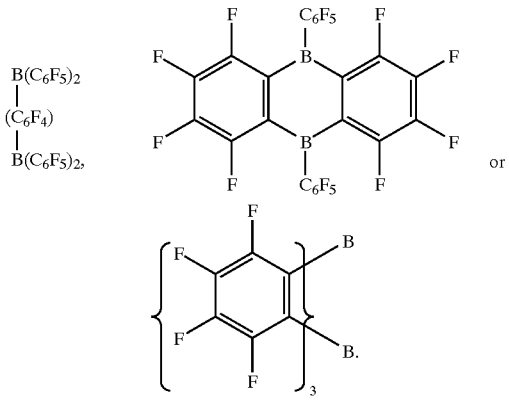

Coordinated to some or all of the Lewis base sites of the Z* anion, that is, to the oxygen or nitrogen atoms, are from 1 to 12 Lewis acids, J*, two or more of which may be joined together in a moiety having multiple Lewis acidic functionality. Each J* group or when two or more J* groups are joined together, the resulting combination, is a neutral compound. Optionally, said J* group may comprise a hydroxyl group or a polar group containing quiescent reactive functionality, so long as such functionality does not interfere with the Lewis acid functionality thereof. Preferably, from 2 to 4 J* groups having from 3 to 100 atoms not counting hydrogen are present in each compound of the invention.

More specific examples of the foregoing Lewis acid compounds, J*, correspond to the formula:

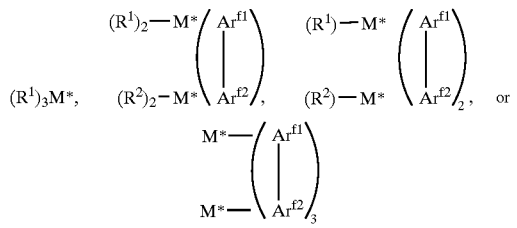

wherein:

M* is aluminum, gallium or boron;

$R^1$ and $R^2$ independently each occurrence are hydride, halide, or a hydrocarbyl, halocarbyl, halohydrocarbyl, dialkylamido, alkoxide, or aryloxide group of up to 20 carbons, optionally substituted with a hydroxyl group or a polar group containing quiescent reactive functionality, and $Ar^{f1}-Ar^{f2}$ in combination, independently each occurrence, is a divalent fluoro-substituted aromatic group of from 6 to 20 carbons, optionally substituted with a hydroxyl group or a polar group containing quiescent reactive functionality.

Highly preferred Lewis acids are aluminum or boron compounds corresponding to the formula: $AlR^1_3$, or $BR^1_3$, wherein $R^1$ independently each occurrence is selected from hydrocarbyl, halocarbyl, and halohydrocarbyl radicals, or such groups further substituted with a hydroxyl group or a polar group containing quiescent reactive functionality, said $R^1$ having up to 20 carbons. In a more highly preferred embodiment, $R^1$ is a $C_{6-20}$ aryl group or a fluorinated $C_{1-20}$ hydrocarbyl group, most preferably, a fluorinated aryl group, especially, pentafluorophenyl.

Preferred examples of the foregoing Lewis acid groups containing multiple Lewis acid sites are:

By the term "polar group containing quiescent reactive functionality" is meant an oxygen, nitrogen, sulfur, or phosphorus containing ligand group that is capped or protected and thereby rendered relatively inert to reaction conditions used in the synthesis or use of the present compounds, but wherein the capping or protecting groups may be later removed, if desired, thereby generating a reactive polar functional group, especially a hydroxyl group or metallated derivative thereof. Suitable reactive polar functional groups include hydroxyl, thiol, amine, and phosphine groups, or hydrocarbyl-, alkali metal- or Bronsted acid salt-derivatives thereof. Suitable quiescent reactive functionality includes the trihydrocarbyllsilyl-, trihydrocarbylgermyl-, dihydrocarbylaluminum-, hydrocarbylzinc- or hydrocarbylmagnesium-functionalized derivative of the foregoing polar groups. Particularly preferred polar containing quiescent reactive functional groups are trihydrocarbylsiloxy, trihydrocarbylsiloxy-substituted hydrocarbyl, dihydrocarbylaluminoxy and dihydrocarbylaluminoxy substituted hydrocarbyl groups. Especially preferred are the trialkylsiloxy- or dialkylaluminoxy-derivatives of such polar functional groups, containing from 1 to 6 carbon in each alkyl group. Especially preferred quiescent reactive functional groups are trimethylsiloxy-groups and diethylaluminoxy-groups.

Such polar group containing quiescent reactive functionality is activated by reaction with a metal hydrocarbyl-, metal halocarbyl-, hydrocarbylmetaloxy- or metal halohydrodarbyl-compound under ligand exchange conditions, thereby producing a neutral hydrocarbon, halohydrocarbon, trimethylsilylhydrocarbon, trimethylsilylhalo-hydrocarbon or trimethylsilylhalocarbon compound as a by-product. The hydroxyl group or polar group containing quiescent reactive functionality may also be employed to react with hydroxyl-, alkylmetal-, hydrocarbylsilyl-, or hydrocarbylsiloxy-functionality of a solid, particulated, support material, optionally after conversion to a metallated or protonated intermediate. This results in tethering or chemically attaching the activator to the surface of the solid, particulated, support material. The resulting substance demonstrates enhanced resistance to loss or removal when exposed to liquids in a polymerization process.

In a preferred embodiment, the foregoing hydroxyl group or polar group containing quiescent reactive functionality is located in the Z* ligand. Examples include hydroxyl, trialkylsiloxy-, trialkylsiloxyalkyl-, trialkylsiloxyaryl-, and dialkylaluminoxyaryl-substituted derivatives of carboxylic acids.

Especially suitable compounds according to the present invention include the tris(pentafluorophenyl)borane-coordinated derivatives of ammonium-, phosphonium-, sulfonium-, oxonium-, carbonium-, silylium-, lead (II)-, silver- or ferrocenium-carboxylates, acetylacetonates, cyclohexa-1,3-dionates or nitrates. Preferred compounds are the ammonium salts, especially those which comprise trihydrocarbyl-substituted ammonium cations, especially trimethylammonium-, triethylammonium-, tripropylammonium-, tri(n-butyl)ammonium-, methyldi (octadecyl)ammonium-, methyldi(tetradecyl)ammonium-, methyl(tetradecyl)(octadecyl)ammonium-, N,N-dimethylanilinium-, N,N-diethylanilinium-, N,N-dimethyl(2,4,6-trimethylanilinium)-, N,N-di(tetradecyl)anilinium-, N,N-di(tetradecyl)-2,4,6-trimethylanilinium)-, N,N-di(octadecyl)lanilinium-, N,N-di(octadecyl)-2,4,6-trimethylanilinium)-, and methyldicyclohexylammonium-cations, or mixtures thereof.

Most preferred ammonium cation containing salts are those containing trihydrocarbyl-substituted ammonium cations containing one or two $C_{10}$–$C_{40}$ alkyl groups, especially methylbis(octadecyl)ammonium- and methylbis(tetradecyl) ammonium-cations. It is further understood that the cation may comprise a mixture of hydrocarbyl groups of differing lengths. For example, the protonated ammonium cation derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Most preferred cocatalysts according to the present invention are the mono- and bis(tris(pentafluorophenyl)borane)-coordinated derivatives of trihydrocarbylammonium stearates, 1,3-cylcohexadionates or acetylacetonates, most especially bis(tris(pentafluorophenyl)borane)-coordinated derivatives of methyldioctyldecylammonium stearate, methylditetradecylammonium stearate, or mixtures thereof, and the bis(tris(pentafluorophenyl)borane)-coordinated derivatives of a reaction product formed by contacting of a trihydrocarbylamine with 1,3-cylcohexadione or acetylacetone, or mixtures thereof, such as the bis(tris(pentafluorophenyl)borane)-coordinated derivatives of a reaction product formed by contacting methyldioctyldecylamine, methylditetradecylamine, or a mixture thereof with 1,3-cylcohexadione, acetylacetone, or a mixture thereof.

The compounds may be prepared by simply combining the Lewis acid, $J^*$, or its Lewis base adduct, such as an ethereate, with the neutral compound corresponding to the cation/anion complex, $(A^{*+a})_b(Z^*)^{-c}{}_d$, or the reaction mixture resulting from contacting a Lewis base, such as an amine, with the Bronsted acid $HZ^*$. They may also be prepared by combination in any order of the Lewis acid, $J^*$, or its Lewis base adduct, such as an etherate, with the protonated version of the conjugated base of the Bronsted acid, $HZ^*$, and optionally a Lewis base, such as an amine, derived from $A^{*+a}$. Additionally, they may be prepared by a condensation reaction between a metal salt of the anion, $Z^*$, and a Lewis acid, $J^*$, preferably under phase transfer conditions, using for example a crown ether to solubilize the metal salt if necessary, followed by a metathesis reaction with the corresponding halide salt of the cation, $A^{*+a}$. Addition of the free base corresponding to the cation, $A^{*+a}$, results in formation of the charge separated species, which may be recovered from the reaction mixture by devolatilization or used without further purification. Finally, they may also be prepared by reaction of a metal salt, especially a silver salt of the anion, $Z^*$ with the corresponding halide salt of the cation, $A^{*+a}$. Addition of the neutral Lewis acid, J, results in formation of the desired product.

If a hydroxyl group or quiescent reactive functionality is present in the compounds of the present invention, or reactive derivatives thereof, they may be readily attached to a reactive substrate, such as a particulated solid containing reactive hydrocarbyl groups, especially hydrocarbylmetal- or hydrocarbylmetalloid-functionality. Examples include alumina, silica, aluminosilicates, and aluminum magnesium silicate materials, containing reactive hydroxyl- or hydrocarbyl-functionality, and such materials treated with any substance to impart reactive metal-hydrocarbyl or metalloid-hydrocarbyl functionality. Examples of such treating substances include trihydrocarbyl aluminum compounds, chlorosilane compounds, and mono- or di-hydrocarbylsilane compounds that react with a portion or all of reactive surface hydroxyl functionality of the substrate to form a "capped" derivative. This technique is known in the art and disclosed for example in U.S. Pat. No. 6,087,293.

Suitable catalysts for use in combination with the foregoing cocatalysts include any compound or complex of a metal of Groups 3–10 of the Periodic Table of the Elements capable of being activated to polymerize ethylenically unsaturated compounds by the present activators. Examples include Group 10 diimine derivatives corresponding to the formula:

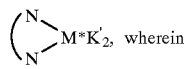

wherein
  $M^*$ is Ni(II) or Pd(II);
  $K'$ is halo, hydrocarbyl, or hydrocarbyloxy;
  and the two nitrogen atoms are linked by a bridging system.

Such catalysts have been previously disclosed in *J. Am. Chem. Soc.*, 118, 267–268 (1996), *J. Am. Chem. Soc.*, 117, 6414–6415 (1995), and *Organometallics*, 16, 1514–1516, (1997).

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, phosphole, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, phosphole, and boratabenzene groups, as well as hydrocarbyl-silyl-(including mono-, di-, or tri(hydrocarbyl) silyl) substituted derivatives thereof. Preferred anionic, delocalized it-bonded groups are cyclopentadienyl, pentamethylcyclopentadienyl, tetramethylcyclopentadienyl, tetramethyl(trimethylsilyl)-cyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands that are boron containing analogues to benzene. They are previously known in the art having been described by G. Herberich, et al., in *Organometallics,* 14,1, 471–480 (1995). Preferred boratabenzenes correspond to the formula:

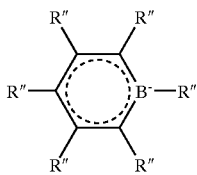

wherein R" is selected from the group consisting of hydrocarbyl, silyl, N,N-dihydrocarbylamino, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Phospholes are anionic ligands that are phosphorus containing analogues to a cyclopentadienyl group. They are previously known in the art having been described by WO 98/50392, and elsewhere. Preferred phosphole ligands correspond to the formula:

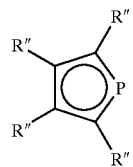

wherein R" is selected from the group consisting of hydrocarbyl, silyl, N,N-dihydrocarbylamino, or germyl, said R" having up to 20 non-hydrogen atoms, and optionally one or more R" groups may be bonded together forming a multicyclic fused ring system, or form a bridging group connected to the metal. In complexes involving divalent derivatives of such delocalized π-bonded groups one atom thereof is bonded by means of a covalent bond or a covalently bonded divalent group to another atom of the complex thereby forming a bridged system.

Phosphinimine/cyclopentadienyl complexes are disclosed in EP-A-890581 and correspond to the formula $[R^{*}]_3$—$P=N]_b M^{}(Cp)(L^1)_{3-b}$, wherein:

$R^{*}$ is a monovalent ligand, illustrated by hydrogen, halogen, or hydrocarbyl, or two $R^{*}$ groups together form a divalent ligand, $M^{**}$ is a Group 4 metal, Cp is cyclopentadienyl, or similar delocalized π-bonded group, $L^1$ is a monovalent ligand group, illustrated by hydrogen, halogen or hydrocarbyl, b is a number from 1 to 3; and n is 1 or 2.

A suitable class of catalysts are transition metal complexes corresponding to the formula:

$Lp_l M X_m X'_n X''_p$, or a dimer thereof wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent group of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, 1+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula $(ER^*_2)_x$, $B(NR^{}_2)$, or $B(NR^{}_2)_2$, wherein E is silicon, germanium, tin, or carbon, R* independently each occurrence is hydrogen or a group selected from silyl, hydrocarbyl, hydrocarbyloxy, and combinations thereof, said R* having up to 30 carbon or silicon atoms, R independently each occurrence is a group selected from silyl, hydrocarbyl, and combinations thereof, said R having up to 30 carbon or silicon atoms, and x is 1 to 8. Preferably, R* independently each occurrence is methyl, ethyl, propyl, benzyl, butyl, phenyl, methoxy, ethoxy, or phenoxy, and R** is methyl, ethyl, propyl, benzyl or butyl.

Examples of the complexes containing two Lp groups are compounds corresponding to the formula:

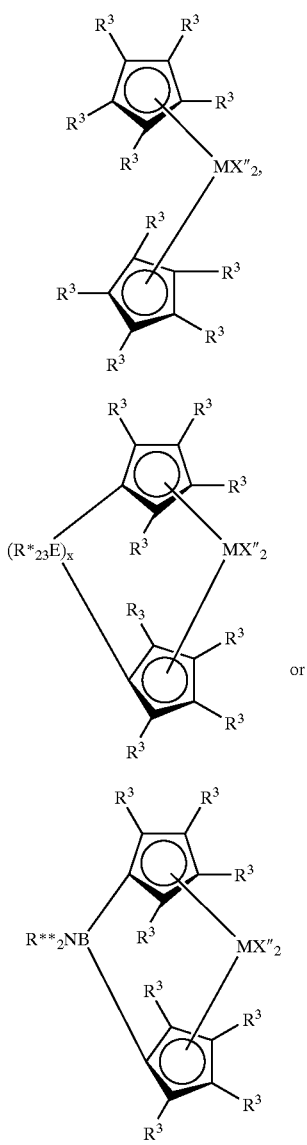

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and
X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and
R*, R**, E and x are as previously defined, preferably $(ER*_2)_x$ is dimethylsilandiyl or ethylene, and $BNR**_2$ is di(isopropyl)aminoborandiyl.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255-6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis (tetramethylcyclopentadienyl)propane, dimethylbis(inden-1-yl)silane, dimethylbis(tetrahydroinden-1-yl)silane, dimethylbis(fluoren-1-yl)silane, dimethylbis(tetrahydrofluoren-1-yl)silane, dimethylbis(2-methyl-4-phenylinden-1-yl)-silane, dimethylbis(2-methylinden-1-yl) silane, di(isopropyl)aminobis(cyclopentadien-1-yl) borandiyl, di(isopropyl)aminobis(2-methyl4-phenylinden-1-yl)-borandiyl, di(isopropyl)aminobis(2-methylinden-1-yl) borandiyl, dimethyl(cyclopentadienyl)(fluoren-1-yl)silane, dimethyl(cyclopentadienyl)(octahydrofluoren-1-yl)silane, dimethyl(cyclopentadienyl)(tetrahydrofluoren-1-yl)silane, (1,1,2,2-tetramethy)-1,2-bis(cyclopentadienyl)disilane, (1,2-bis(cyclopentadienyl)ethane, and dimethyl (cyclopentadienyl)-1-(fluoren-1-yl)methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

Complexes containing two Lp groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide, bis (cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl) zirconiummethylmethoxide,
bis(pentamethylcyclopentadienyl)zirconiummethylchloride,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl, bis(trimethylsilylcyclopentadienyl)zirconiumdibenzyl,
dimethylsilyl-bis(cyclopentadienyl)zirconiumdimethyl,
dimethylsilyl-bis(tetramethylcyclopentadienyl)titanium (III) allyl
dimethylsilyl-bis(t-butylcyclopentadienyl) zirconiumdibenzyl,
dimethylsilyl-bis(n-butylcyclopentadienyl)zirconium bis(trimethylsilyl),
(methylene-bis(tetramethylcyclopentadienyl)titanium(III)2-(dimethylamino)benzyl,
(methylene-bis(n-butylcyclopentadienyl)titanium(III)2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium (II)1,4-diphenyl-1,3-butadiene,
di(isopropylamino)borandiylbis(2-methyl-4-phenylindenyl) zirconium dimethyl,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

A further class of metal complexes utilized in the present invention corresponds to the preceding formula $Lp_{pl}MX_mX'_nX''_p$, or a dimer thereof, wherein X is a divalent group of up to 50 non-hydrogen atoms that together with Lp forms a metallocycle with M.

Preferred divalent X groups include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

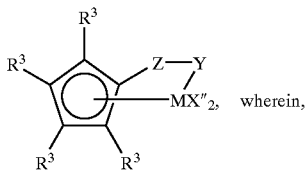 wherein, wherein,
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system,
each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*-, —PR*-; and
Z is $SiR*_2$, $CR*_2$, $SiR*_2SiR*_2$, $CR*_2CR*_2$, $CR*=CR*$, $CR*_2SiR*_2$, $GeR*_2$, or $B(NR**_2)$ wherein R* and R** are as previously defined.

Illustrative Group 4 metal complexes of the latter formula that may be employed in the practice of the present invention include:
cyclopentadienyltitaniumtrimethyl,
indenyltitaniumtrimethyl,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-η-1,4,5,6,7,8-hexahydronaphthalenyl) dimethylsilanetitaniumdimethyl,
(tert-butylamido)(1,1,2,3-tetramethyl-2,3,4,9,10-η-1,4,5,6,7,8-hexahydronaphthalenyl) dimethylsilanetitaniumdim
(tert-butylamido)(tetramethyl-η⁵-cyclopentadienyl) dimethylsilanetitanium dibenzyl,
(tert-butylamido)(tetramethyld-η⁵-cyclopentadienyl) dimethylsilanetitanium dimethyl,
(tert-butylamido)(tetramethyl-η⁵-cyclopentadienyl)-1,2-ethanediyltitanium dimethyl,
(tert-butylamido)(tetramethyl-η⁵-indenyl) dimethylsilanetitanium dimethyl,
(tert-butylamido)(tetramethyl-η⁵-cyclopentadienyl) dimethylsilane titanium (III) 2-(dimethylamino)benzyl;
(tert-butylamido)(tetramethyl-η⁵-cyclopentadienyl) dimethylsilanetitanium (III)allyl,
(tert-butylamido)(tetramethyl-η⁵-cyclopentadienyl) dimethylsilanetitanium (III) 2,4-dimethylpentadienyl,
(tert-butylamido)(tetramethyl-η⁵-cyclopentadienyl) dimethylsilanetitanium (II) 1,4-diphenyl-1,3-butadiene,
(tert-butylamido)(tetramethyl-η⁵-cyclopentadienyl) dimethylsilanetitanium (II) 1,3-pentadiene,
(tert-butylamido)(2-methylindenyl)dimethylsilanetitanium (II)1,4-diphenyl-1,3-butadiene,
(tert-butylamido)(2-methylindenyl)dimethylsilanetitanium (II)2,4-hexadiene,
(tert-butylamido)(2-methylindenyl)dimethylsilanetitanium (IV)2,3-dimethyl-1,3-butadiene,
(tert-butylamido)(2-methylindenyl)dimethylsilanetitanium (I)isoprene,
(tert-butylamido)(2-methylindenyl)dimethylsilanetitanium (IV)1,3-butadiene,
(tert-butylamido)(2,3-dimethylindenyl) dimethylsilanetitanium (IV) 2,3-dimethyl-1,3-butadiene,
(tert-butylamido)(2,3-dimethylindenyl) dimethylsilanetitanium (IV)isoprene
(tert-butylamido)(2,3-dimethylindenyl) dimethylsilanetitanum (IV)dimethyl
(tert-butylamido)(2,3-dimethylindenyl) dimethylsilanetitanium (IV)dibenzyl
(tert-butylamido)(2,3-dimethylindenyl) dimethylsilanetitanium (IV)1,3-butadiene,
(tert-butylamido)(2,3-dimethylindenyl) dimethylsilanetitanium (II)1,3-pentadiene,
(tert-butylamido)(2,3-dimethylindenyl) dimethylsilanetitanium (II),4-diphenyl-1,3-butadiene,
(tert-butylamido)(2-methylindenyl)dimethylsilanetitanium (IV)1,3-pentadiene,
(tert-butylamido)(2-methylindenyl)dimethylsilanetitanium (IV)dimethyl,
(tert-butylamido)(2-methylindenyl)dimethylsilanetitanium (IV)dibenzyl,
(tert-butylamido)(2-methyl-4-phenylindenyl) dimethylsilanetitanium (II)1,4-diphenyl-1,3-butadiene,
(tert-butylamido)(2-methyl-4-phenylindenyl) dimethylsilanetitanium (II)1,3-pentadiene, (tert-butylamido)(2-methyl-4-phenylindenyl) dimethylsilanetitanium (II)2,4-hexadiene,
(tert-butylamido)(tetramethyl-$\eta^5$-cyclopentadienyl) dimethyl-silanetitanium (IV) 1,3-butadiene,
(tert-butylamido)(tetramethyl-$\eta^5$-cyclopentadienyl) dimethylsilanetitanium (IV) 2,3-dimethyl-1,3-butadiene,
(tert-butylamido)(tetramethyl-$\eta^5$-cyclopentadienyl) dimethylsilanetitanium (IV) isoprene,
(tert-butylamido)(tetramethyl-$\eta^5$-cyclopentadienyl) dimethyl-silanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethyl-silanetitanium (II) 3-methyl-1,3-pentadiene,
(tert-butylamido)(2,4-dimethylpentadien-3-yl) dimethylsilanetitaniumdimethyl,
(tert-butylamido)(6,6-dimethylcyclohexadienyl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl
(tert-butylamido)(tetramethyl-$\eta^5$-cyclopentadienyl methylphenylsilanetitanium (IV) dimethyl,
(tert-butylamido)(tetramethyl-$\eta^5$-cyclopentadienyl methylphenylsilanetitanium (II) 1,4-diphenyl-1,3-butadiene,
1-(tert-butylamido)-2-(tetramethyl-$\eta^5$-cyclopentadienyl) ethanediyltitanium (IV) dimethyl,
1-(tert-butylamido)-2-(tetramethyl-$\eta^5$-cyclopentadienyl) ethanediyl titanium (II)1,4-diphenyl-1,3-butadiene,
(tert-butylamido)(3-(N-pyrrolyl)indenyl) dimethylsilanetitanium (IV)2,3-dimethyl-1,3-butadiene,
(tert-butylamido)(3-(N-pyrrolyl)indenyl) dimethylsilanetitanium (IV)isoprene
(tert-butylamido)(3-(N-pyrrolyl)indenyl) dimethylsilanetitanium (IV)dimethyl
(tert-butylamido)(3-(N-pyrrolyl)indenyl) dimethylsilanetitanium (IV)dibenzyl
(tert-butylamido)(3-(N-pyrrolyl)indenyl) dimethylsilanetitanium (IV)1,3-butadiene,
(tert-butylamido)(3-(N-pyrrolyl)indenyl) dimethylsilanetitanium (II)1,3-pentadiene,
(tert-butylamido)(3-(N-pyrrolyl)indenyl) dimethylsilanetitanium (II)1,4-diphenyl-1,3-butadiene, and
(tert-butylamido)(3-N-pyrrolidinylinden-1-yl) dimethylsilanetitanium (IV)dimethyl.

Other catalysts, especially catalysts containing other Group 4 metals, will, of course, be apparent to those skilled in the art. Most highly preferred metal complexes for use herein are the following metal complexes:
(t-butylamido)dimethyl(tetramethylcyclopentadienyl) silanetitanium dimethyl,
(t-butylamido)dimethyl(tetramethylcyclopentadienyl) silanetitanium (II)1,3-pentadiene,
(t-butylamido)dimethyl(tetramethylcyclopentadienyl) silanetitanium (II)1,4 diphenyl-1,3-butadiene,
(cyclohexylamido)dimethyl(tetramethylcyclopentadienyl) silanetitanium dimethyl,
cyclohexylamido)dimethyl(tetramethylcyclopentadienyl) silanetitanium (II)1,3-pentadiene,
cyclohexylamido)dimethyl(tetramethylcyclopentadienyl) silanetitanium (II)1,4 diphenyl-1,3-butadiene,
(cyclododecylamido)dimethyl (tetramethylcyclopentadienyl)silanetitanium dimethyl,
(cyclododecylamido)dimethyl (tetramethylcyclopentadienyl)silanetitanium (II)1,3-pentadiene,
(cyclododecylamido)dimethyl (tetramethylcyclopentadienyl)silanetitanium (II)1,4 diphenyl-1,3-butadiene,
(t-butylamido)dimethyl(2-methyl-s-indacen-1-yl) silanetitanium dimethyl,
(t-butylamido)dimethyl(2-methyl-s-indacen-1-yl) silanetitanium (II)1,3-pentadiene,
(t-butylamido)dimethyl(2-methyl-s-indacen-1-yl) silanetitanium (II)1,4 diphenyl-1,3-butadiene,
(cyclohexylamido)dimethyl(2-methyl-s-indacen-1-yl) silanetitanium dimethyl,
cyclohexylamido)dimethyl(2-methyl-s-indacen-1-yl) silanetitanium (II)1,3-pentadiene,
cyclohexylamido)dimethyl(2-methyl-s-indacen-1-yl) silanetitanium(II)1,4 diphenyl-1,3-butadiene,
(cyclododecylamido)dimethyl(2-methyl-s-indacen-1-yl) silanetitanium dimethyl,
(cyclododecylamido)dimethyl(2-methyl-s-indacen-1-yl) silanetitanium(II)1,3-pentadiene,
(cyclododecylamido)dimethyl(2-methyl-s-indacen-1-yl) silanetitanium(II)1,4 diphenyl-1,3-butadiene,
(t-butylamido)dimethyl(3,4-(cyclopenta(l)phenanthren-1-yl)silanetitanium dimethyl,
(t-butylamido)dimethyl(3,4-(cyclopenta(l)phenanthren-1-yl)silanetitanium(II)1,3-pentadiene,
(t-butylamido)dimethyl(3,4-(cyclopenta(l)penanthren-1-yl) silanetitanium(II)1,4-diphenyl-1,3-butadiene,
(cyclohexylamido)dimethyl(3,4-(cyclopenta(l)phenanthren-1-yl)silanetitanium dimethyl,
cyclohexylamido)dimethyl(3,4-(cyclopenta(l)phenanthren-1-yl)silanetitanium(II)1,3-pentadiene,
cyclohexylamido)dimethyl(3,4-(cyclopenta(l)phenanthren 1-yl)silanetitanium(II)1,4 diphenyl-1,3-butadiene,
(cyclododecylamido)dimethyl(3,4-(cyclopenta(l) phenanthren-1-yl)silanetitanium dimethyl,
(cyclododecylamido)dimethyl(3,4-(cyclopenta(l) phenanthren-1-yl)silanetitanium(II)1,3-pentadiene,
(cyclododecylamido)dimethyl(3,4-(cyclopenta(l) phenanthren-1-yl)silanetitanium(II)1,4 diphenyl-1,3-butadiene,
(t-butylamido)dimethyl(2-methyl-4-phenylinden-1-yl) silanetitanium dimethyl,
(t-butylamido)dimethyl(2-methyl-4-phenylinden-1-yl) silanetitanium(II)1,3-pentadiene,
(t-butylamido)dimethyl(2-methyl-4-phenylinden-1-yl) silanetitanium(II)1,4-diphenyl-1,3-butadiene,
(cyclohexylamido)dimethyl(2-methyl-4-phenylinden-1-yl) silanetitanium dimethyl,
cyclohexylamido)dimethyl(2-methyl-4-phenylinden-1-yl) silanetitanium(II)1,3-pentadiene,
cyclohexylamido)dimethyl(2-methyl-4-phenylinden-1-yl) silanetitanium(II)1,4-diphenyl-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II)1,3-pentadiene,
(cyclododecylamido)dimethyl(2-methyl-4-phenylinden-1-yl)silanetitanium(II)1,4-diphenyl-1,3-butadiene,
(t-butylamido)dimethyl(2-methyl-4-phenylinden-1-yl) silanetitanium dimethyl,
(t-butylamido)dimethyl(2-methyl-4-phenylinden-1-yl) silanetitanium (II)1,3-pentadiene,
(t-butylamido)dimethyl(2-methyl-4-phenylinden-1-yl) silanetitanium (II)1,4 diphenyl-1,3-butadiene, (cyclohexylamido)dimethyl(2-methyl-4-phenylinden-1-yl) silanetitanium dimethyl,
cyclohexylamido)dimethyl(2-methyl-4-phenylinden-1-yl) silanetitanium(II)1,3-pentadiene,
cyclohexylamido)dimethyl(2-methyl-4-phenylinden-1-yl) silanetitanium(II)1,4 dipheney-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II)1,3-pentadiene,
(cyclododecylamido)dimethyl(2-methyl-4-phenylinden-1-yl)silanetitanium(II)1,4 diphenyl-1,3-butadiene,
(t-butylamido)dimethyl(3-(1-pyrrolidinyl)inden-1-yl) silanetitanium dimethyl,
(t-butylamido)dimethyl(3-(1-pyrrolidinyl)inden-1-yl) silanetitanium(II)1,3-pentadiene,
(t-butylamido)dimethyl(3-(1-pyrrolidinyl)inden-1-yl) silanetitanium(II)1,4 diphenyl-1,3-butadiene,
(cyclohexylamido)dimethyl(3-(1-pyrrolidinyl)inden-1-yl) silanetitanium dimethyl,
cyclohexylamido)dimethyl(3-(1-pyrrolidinyl)inden-1-yl) silanetitanium(II)1,3-pentadiene,
cyclohexylamido)dimethyl(3-(1-pyrrolidinyl)inden-1-yl) silanetitanium(II)1,4 diphenyl-1,3-butadiene,
(cyclododecylamido)dimethyl(3-(1-pyrrolidinyl)inden-1-yl) silanetitanium dimethyl,
(cyclododecylamido)dimethyl(3-(1-pyrrolidinyl)inden-1-yl) silanetitanium(II)1,3-pentadiene,
(cyclododecylamido)dimethyl(3-(1-pyrrolidinyl)inden-1-yl) silanetitanium(II)1,4 diphenyl-1,3-butadiene,
(t-butylamido)dimethyl(3-(1-pyrrolidinyl)inden-1-yl) silanetitanium dimethyl,
(t-butylamido)dimethyl(3-(1-pyrrolidinyl)inden-1-yl) silanetitanium (II)1,3-pentadiene,
(t-butylamido)dimethyl(3-(1-pyrrolidinyl)inden-1-yl) silanetitanium (II)1,4 diphenyl-1,3-butadiene,
(cyclohexylamido)dimethyl(3-(1-pyrrolidinyl)inden-1-yl) silanetitanium dimethyl,
cyclohexylamido)dimethyl(3-(1-pyrrolidinyl)inden-1-yl) silanetitanium(II)1,3-pentadiene,
cyclohexylamido)dimethyl(3-(1-pyrrolidinyl)inden-1-yl) silanetitanium(II)1,4 diphenyl-1,3-butadiene,
(cyclododecylamido)dimethyl(3-(1-pyrrolidinyl)inden-1-yl) silanetitanium dimethyl,
(cyclododecylamido)dimethyl(3-(1-pyrrolidinyl)inden-1-yl) silanetitanium(II)1,3-pentadiene,
(cyclododecylamido)dimethyl(3-(1-pyrrolidinyl)inden-1-yl) silanetitanium(II)1,4 diphenyl-1,3-butadiene,
1,2-ethanebis(inden-1-yl)zirconium dimethyl,
1,2-ethanebis(inden-1-yl)zirconium(II)1,3-pentadiene,
1,2-ethanebis(inden-1-yl)zirconium(II)1,4 diphenyl-1,3-butadiene,
1,2-ethanebis(2-methyl-4-phenylinden-1-yl)zirconium dimethyl,
1,2-ethanebis(2-methyl-4-phenylinden-1-yl)zirconium(II)1,3-pentadiene,
1,2-ethanebis(2-methyl-4-phenylinden-1-yl)zirconium(II) 1,4 diphenyl-1,3-butadiene, dimethylsilanebis(inden-1-yl)zirconium dimethyl,
dimethylsilanebis(inden-1-yl)zirconium(II)1,3-pentadiene,
dimethylsilanebis(inden-1-yl)zirconium(II)1,4 diphenyl-1,3-butadiene,
dimethylsilanebis(2-methyl-4-phenylinden-1-yl)zirconium dimethyl,
dimethylsilanebis(2-methyl-4-phenylinden-1-yl)zirconium (II)1,3-pentadiene, and
dimethylsilanebis(2-methyl-4-phenylinden-1-yl)zirconium (II 1,4 diphenyl-1,3-butadiene.

The cocatalysts of the invention may be, and preferably are used in combination with an oligomeric or polymeric alumoxane compound, a tri(hydrocarbyl)aluminum compound, a di(hydrocarbyl)(hydrocarbyloxy)aluminum compound, a di(hydrocarbyl)(dihydrocarbyl-amido) aluminum compound, a bis(dihydrocarbyl-amido) (hydrocarbyl)aluminum compound, a di(hydrocarbyl)amido (disilyl)aluminum compound, a di(hydrocarbyl)-amido (hydrocarbyl)(silyl)aluminum compound, a bis (dihydrocarbylamido)(silyl)aluminum compound, or a mixture of the foregoing compounds, having from 1 to 20 non-hydrogen atoms in each hydrocarbyl, hydrocarbyloxy, or silyl group, if desired. These aluminum compounds are usefully employed for their beneficial ability to scavenge impurities such as oxygen, water, and aldehydes from the polymerization mixture as well as to react with the hydroxyl group or quiescent reactive functionality of the compounds or the reactive derivatives thereof.

Preferred aluminum compounds include $C_{1-20}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methlphenoxy) diisobutylaluminum), methylalumoxane, modified methalumoxane, especially isobutyl modified alumoxane, and tri(ethylaluminum)-, tris (pentafluorophenyl)borane-, or tris(pentafluorophenyl) aluminum-modified alumoxanes or supported derivatives thereof. (The latter compositions are previously known, having been disclosed in WO99/15534. Additional species include mixtures of aluminum containing Lewis acids as disclosed in U.S. Pat. No. 6,214,760 and U.S. Pat. No. 6,211,111. The molar ratio of activator to aluminum compound is preferably from 1:10,000 to 1000:1, more preferably from 1:5000 to 100:1, most preferably from 1:100 to 100:1.

The equivalent ratio of catalyst/cocatalyst (calculated based on quantity of metal in the catalyst and anionic charges on the cocatalyst employed preferably ranges from 1:10 to 10:1, more preferably from 1:5 to 2:1, most preferably from 1:4 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, vinylbenzocyclobutene, 1,4-hexadiene, dicyclopentadiene, ethylidene norbomene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Suitable processing conditions include solution polymerization, more preferably continuous solution polymerization processes, conducted in the presence of an aliphatic or alicyclic liquid diluent, preferably using the unsupported, quiescent reactive functionality containing compounds. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof, and perfluorinated hydrocarbons such as perfluorinated $C_{4-10}$ alkanes, and the like. Suitable diluents also include aromatic hydrocarbons (particularly for use with aromatic a-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}$:1 to 0.1:1, more preferably from $10^{-12}$:1 to $10^{-5}$:1.

The catalyst composition of the invention may also be utilized in combination with at least one additional homogeneous or heterogeneous polymerization catalyst in the same reactor or in separate reactors connected in series or in parallel to prepare polymer blends having desirable properties.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution cc-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from 3 to 8, preferably from 3 to 6 carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed.

The polymerization reaction occurring in the gas fluidized bed is catalyzed by the continuous or semi-continuous addition of catalyst. Such catalyst can be supported on an inorganic or organic support material if desired. Direct addition of the catalyst in the form of a solution in a solvent to a gas-phase polymerization reactor may be employed as well. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

Slurry polymerization conditions and supported catalyst preparation techniques for use therein are well known from the published literature. Generally such catalysts are prepared by the same techniques as are employed for making supported catalysts used in gas phase polymerizations. Slurry polymerization conditions generally encompass polymerization of a $C_{2-20}$ olefin, diolefin, cycloolefin, or mixture thereof in an aliphatic solvent at a temperature below that at which the polymer is readily soluble in the presence of a supported catalyst. Slurry phase processes particularly suited for the polymerization of $C_{2-6}$ olefins, especially the homopolymerization and copolymerization of ethylene and propylene, and the copolymerization of ethylene with $C_{3-8}$ α-olefins such as, for example, 1-butene, 1-hexene, 4-methyl-1-pentene and 1-octene are well known in the art. Such processes are used commercially on a large scale for the manufacture of high density polyethylene (HDPE), medium density polyethylene (MDPE), linear low density polyethylene (LLDPE) and polypropylene, especially isotactic polypropylene.

In addition to the foregoing techniques for coordination addition polymerizations, the present compounds and compositions disclosed herein are useful as initiators or catalysts in the field of cationic polymerization. Preferred monomers for such cationic polymerizations include styrene, α-methylstyrene, ring alkyl-substituted styrene, isobutylene, and mixtures thereof. Preferred temperatures for cationic polymerizations are from −100 to 50° C., preferably −80 to 20° C.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of 20–25° C., and "mixed alkanes" refers to a mixture of mostly $C_6$–$C_{12}$ alkanes available commercially under the trademark Isopar E™ from Exxon Chemicals Inc.

All manipulation of air sensitive materials was performed in an argon filled, vacuum atmospheres, glove box or on a high vacuum line using standard Shlenk techniques. Toluene was purified by passage through columns packed with activated alumina (Kaiser A-2) and supported copper (Engelhard, Cu-0224 S). Hexanes were purified by distillation from sodium benzophenone ketyl. Tris (pentafluorophenyl)borane (FAB) was purchased from Boulder Scientific. Dioctadecylmethylamine is a bis (hydrogenated tallow) alkylamine of approximate formulation $(C_{18}H_{35})_2CH_3N$, available commercially under the tradename Armeen™ M2HT from Akzo Nobel, Inc., and was used as received.

Example 1

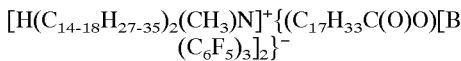

A) Synthesis of $[H(C_{14-18}H_{27-35})_2(CH_3)N]^+[(C_{17}H_{33}C(O)O]^-$

To a flask containing 533 mg (1.87 mmol) of stearic acid 1000 mg (1.87 mmol) of Armeen™ M2HT and 25 g of hexane were added. The reaction mixture was warmed until a clear solution resulted. After 30 minutes of stirring the volatiles were removed under vacuum, leaving the desired product as a white solid.

B) Synthesis of $[H(C_{14-18}H_{27-35})_2(CH_3)N]^+\{(C_{17}H_{33}C(O)O)[B(C6F_5)_3]_2\}^-$ A flask containing FAB (123 mg, 0.24 mmol) and 20 ml of toluene was charged with 99 mg (0.12 mmol) of the ammonium stearate salt prepared in step A). A clear, 0.006 molar solution of the desired complex for use in polymerization resulted.

Example 2

The reaction conditions of Example 1 were substantially repeated, excepting that the ammonium stearate salt was not isolated before addition of 2 equivalents of FAB. A clear, toluene solution of the desired product resulted. Example 3

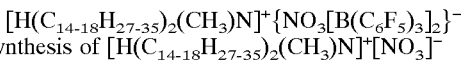

A) Synthesis of $[H(C_{14-18}H_{27-35})_2(CH_3)N]^+[NO_3]^-$

To a flask containing 277 mg of silver nitrate suspended in 35 g hexane, 932 mg of the hydrochloride salt of Armeen™ M2HT were added. The mixture was heated to 40° C. for 15 minutes, cooled to room temperature and sonicated for 2 hours, then stirred an additional 48 hours. The reaction mixture was warmed again to 40° C. and filtered through a pad of diatomaceous earth. The filtrate containing the desired product was retained.

B) Synthesis of $[H(C_{14-18}H_{27-35})_2(CH_3)N]^+\{(NO_3)[B(C_6F_5)_3]_2\}^-$

FAB (2.5 g, 4.8 mmol) was added to the filtrate obtained from step A). After 1 hour, all volatiles were removed under reduced pressure. The resulting product was redissolved in toluene to give a clear, 0.006 M solution of the desired product for use in polymerization.

Example 4

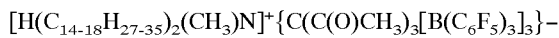

Methyl triacetyl (HC(C(O)CH$_3$)$_3$, 17 mg, 0.13 mmoles) and Armeen™ M2HT ((C$_{14-18}$H$_{27-35}$)$_2$(CH$_3$)N, 64 mg, 0.13 mmoles) were combined in 10 ml of toluene. After 15 minutes, FAB, (6.082 g of a 3.03 weight percent solution in mixed alkanes, 0.36 mmole) was added. After 10 minutes stirring another 1.0 ml of toluene was added to give a 0.006 molar solution which was used as a polymerization catalyst solution without further modification.

Example 5

Indan-1,3-dione (C$_9$O$_2$H$_6$, 17 mg, 0.12 mmoles) and Armeen™ M2HT ((C$_{14-18}$H$_{27-35}$) $_2$(CH$_3$)N, 64 mg, 0.13 mmoles) were combined in 10 ml of toluene. After 15 minutes, FAB, (4.055 g of a 3.03 weight percent solution in mixed alkanes, 0.24 mmole) was added. After 10 minutes stirring another 4.2 ml of toluene was added to give a 0.006 molar solution which was used as a polymerization catalyst solution without further modification.

Polymerizations

Mixed alkanes and liquid olefins are purified by sparging with purified nitrogen followed by passage through columns containing alumina (A-2, available from LaRoche Inc.) and Q5 reactant (available from Englehard Chemicals Inc.) at 50 psig (450 kPa) using a purified nitrogen pad. All transfers of solvents and solutions described below are accomplished using a gaseous pad of dry, purified nitrogen or argon. Gaseous feeds to the reactor are purified by passage through columns of A-204 alumina (available from LaRoche Inc.) and Q5 reactant. The aluminas are previously activated by treatment at 375° C. with nitrogen, and Q5 reactant is activated by treatment at 200° C. with 5 percent hydrogen in nitrogen.

A stirred, two-liter Parr reactor was charged with approximately 433 g of toluene and 455 g of 1-octene comonomer. Hydrogen was added as a molecular weight control agent by differential pressure expansion from a 75 mL addition tank at 50 psig (450 kPa). The reactor was heated to 90° C. and saturated with ethylene at 200 psig (1.4 MPa). The appropriate amount of catalyst, tetramethylcyclopentadienyl) dimethyl(t-butylamido)silane titanium (II) 1,3-pentadiene and cocatalyst (either an example of the invention or a comparative cocatalyst, dioctadecylmethylammonium tetrakis(pentafluorophenyl)borate, DAB) in toluene were premixed in a glovebox in a 1:1.1 molar ratio and transferred to a catalyst addition tank and injected into the reactor. (Periodic additions of catalyst/cocatalyst solution may be added during the course of the run.) The polymerization conditions were maintained during the run with ethylene on demand.

The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation). Polymers formed are dried in a programmed vacuum oven with a maximum temperature of 140° C. and a 20 hour heating period. Results of the polymerization are reported in Table 1.

TABLE 1

| Run | Cocatalyst | Max $C_2H_4$ flow (g/min) | Efficiency[2] |
|---|---|---|---|
| 1* | DAB[1] | 31.8 | 1.8 |
| 2* | " | 31.8 | 1.8 |
| 3 | Ex. 1 | 39.3 | 2.7 |
| 4 | " | 31.8 | 2.4 |
| 5* | DAB | 24.9 | 1.8 |
| 6* | " | 27.8 | — |
| 7 | Ex. 3 | 30.7 | — |
| 8 | " | 19.2 | — |
| 9* | DAB | 24.7 | — |
| 10* | " | 14.8 | 1.5 |
| 11 | Ex. 4 | 23.7 | 1.6 |
| 12 | " | 26.2 | 1.7 |
| 13 | Ex. 5 | 30.6 | 2.0 |
| 14 | " | 30.1 | 2.0 |
| 15* | DAB | 13.4 | 1.3 |

*comparative, not an example of the invention

TABLE 1-continued

| Run | Cocatalyst | Max $C_2H_4$ flow (g/min) | Efficiency[2] |
|---|---|---|---|

[1]dioctadecylmethylammonium tetrakis(pentafluorophenyl)borate
[2]efficiency, g polymer/µg Ti

What is claimed is:

1. A polymerization process comprising contacting one or more α-olefins under polymerization conditions with a catalyst composition comprising the combination or reaction product resulting from combining, 1) a Group 3–10 or Lanthanide metal complex.

2) a compound corresponding to the formula: $(A^{*+a})_b (Z^*J^*_j)^{-c}_d$, wherein:

A* is a proton or a cation of from 1 to 80 atoms, not counting hydrogen atoms, said A* having a charge+ a;

Z* is an anion group of from 1 to 50 atoms, not counting hydrogen atoms, further containing two or more Lewis base sites, said Z* being the conjugate base of an inorganic Bronsted acid or a carbonyl- or non-cyclic, imino-group containing organic Bronsted acid;

J* independently each occurrence is a Lewis acid of from 1 to 80 atoms, not counting hydrogen atoms, coordinated to at least one Lewis base site of Z*, and optionally two or more such J* groups may be joined together in a moiety having multiple Lewis acidic functionality;

j is a number from 1 to 12; and a, b, c, and d are integers from 1 to 3, with the proviso that a×b is equal to c×d;

3) optionally an organoaluminum compound, and 4) further optionally, a solid, particulated support.

2. A polymerization process according to claim 1 that is a solution polymerization.

3. A polymerization process according to claim 1 that is a gas phase polymerization.

4. A polymerization process according to claim 1 that is a slurry polymerization.

5. A polymerization process according to claim 1 that is a cationic polymerization.

6. A process according to claim 1 if wherein Z* is selected from the group consisting of: $NO_3^-$, $PO_4^{3-}$. $SO_4^{2-}$, $RSO_3^-$, $CO_3^{2-}$, [RC(O)O]$^-$, [RC(NR)NR]$^-$, [R'C(O)CR'C(O)R']$^-$, [(R'C(O))_3C]$^-$, [RC(NR)CRC(NR)R]$^-$, and [(RC(NR))_3C]$^-$, wherein each R is independently a hydrogen-; hydrocarbyl-; or halocarbyl-group; a hydrocarbyl group further substituted with one or more carbonyl-, halo-, hydroxy-, dialkylamino-, dialkylaluminumoxy-, trihydrocarbylsilyl-, trihydrocarbylsiloxy-, or hydrocarbyloxy-groups; or a halocarbyl group further substituted with one or more carbonyl-, hydroxy-, dialkylamino-, dialkylaluminumoxy-, trihydrocarbylsilyl-, trihydrocarbylsiloxy-, or hydrocarbyloxy-groups; and each R' is independently R or two R' groups may be joined together thereby forming a divalent group.

7. A process according to claim 1 wherein Z* is an acetylacetonate, cyclohexa-1,3-dionate, [RC(O)O]$^-$ or $NO_3^{-2}$, wherein R is a $C_{6-24}$ hydrocarbyl group, most preferably a $C_{12-24}$ alkyl group, or an indane-1,3-dione anion or methyl triacetyl anion of the following structure:

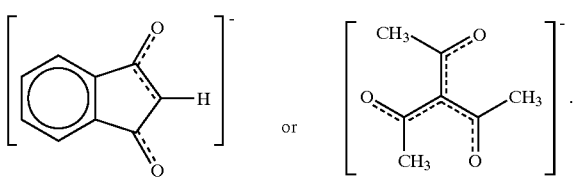

8. A process according to claim 1 wherein $A^{*+a}$ is a proton or is selected from the group consisting of ammonium, sulfonium, phosphonium, oxonium, carbonium, silylium, ferrocenium, $Ag^+$, and $Pb^{+2}$ cations.

9. A process according to claim 1, wherein $A^{*+a}$ is a trimethylammonium-, triethylammonium-, tripropylammonium-, tri(n-butyl) ammonium-, methyldi($C_{14-18}$ alkyl)ammonium-, dimethyl($C_{14-18}$ alkyl) ammonium-, N,N-dimethylanilinium-, N,N-diethylanilinium-, N,N-dimethyl(2,4,6-trimethylanilinium)-, N,N-di(tetradecyl)lanilinium-, N,N-di(tetradecyl) (2,4,6-trimethylanilinium)-, N,N-di(octadecyl)lanilinium-, N,N-di(octadecyl)-2,4,6-trimethylanilinium)-, or methyldicyclohexylammonium-cation.

10. A process according to claim 1 wherein $J^{*'}$ is tris(pentafluorophenyl)borane or tris(pentafluorophenyl) alumane).

11. A process according to claim 1 wherein compound 2) is a bis(tris(pentafluorophenyl)borane)-coordinated derivative of a trihydrocarbylammonium stearate or a mono(tris(pentafluorophenyl)-borane)-coordinated derivative of a trihydrocarbylammonium stearate.

12. A process according to claim 1 wherein an organoaluminum compound is included in the catalyst composition.

13. A process according to claim 13 wherein the organoaluminum compound is an alumoxane.

14. A process according to claim 14 wherein a solid, particulated support is present.

15. A process according to claim 1 wherein component 1) is a Group 4 metal complex.

* * * * *